US006103233A

United States Patent [19]
Pouletty et al.

[11] Patent Number: 6,103,233
[45] Date of Patent: *Aug. 15, 2000

[54] CELLULAR AND SERUM PROTEIN ANCHORS AND CONJUGATES

[75] Inventors: Philippe Pouletty; Christine Pouletty, both of Atherton, Calif.

[73] Assignee: Conjuchem, Inc., Montreal, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/477,900

[22] Filed: Jun. 7, 1995

Related U.S. Application Data

[63] Continuation of application No. 08/237,346, May 3, 1994, Pat. No. 5,612,034, which is a continuation-in-part of application No. 08/137,821, Oct. 15, 1993, abandoned, which is a continuation-in-part of application No. 08/070,092, May 27, 1993, abandoned, which is a continuation-in-part of application No. 07/592,214, Oct. 3, 1990, abandoned.

[51] Int. Cl.$^7$ .................. A61K 39/395; C07K 16/18; C07K 16/28; C07K 16/44
[52] U.S. Cl. .................. 424/133.1; 424/136.1; 424/153.1; 424/173.1; 424/175.1; 530/387.3; 530/388.7; 530/388.85; 530/388.9; 530/389.6; 530/389.1; 530/389.8
[58] Field of Search .................. 530/387.1, 402, 530/387.3, 388.7, 388.85, 388.9, 389.6, 389.1, 389.8; 424/133.1, 136.1, 153.1, 173.1, 175.1

[56] References Cited

U.S. PATENT DOCUMENTS

| | | | |
|---|---|---|---|
| 4,676,980 | 6/1987 | Segal et al. | 424/85 |
| 5,612,034 | 3/1997 | Pouletty et al. | |
| 5,843,440 | 12/1998 | Pouletty et al. | |

FOREIGN PATENT DOCUMENTS

| | | |
|---|---|---|
| 0323806 | 12/1989 | European Pat. Off. |
| 0 602 290 A1 | 4/1992 | European Pat. Off. |

OTHER PUBLICATIONS

Christian, J. et al; Senescence of Canine Biotinylated Erythrocytes: Increased Autologous Immunoglobulin Binding Occurs on Erythrocytes Aged In Vivo for 104 to 110 Days, Blood, vol. 82, No. 11, pp. 3469–3473 (1993).
Coller, B. et al, Thromboerythrocytes, J. Clin. Invest. vol. 89, pp. 546–555, (1992).
Gilles, S. et al; Antigen biding and biological activities of engineered mutant chimeric antibodies with human tumor specificities; Hum. Antibod. Hybridomas vol. 1, No. 1 pp. 47–54 (1990).
Harris, W. et al; Therapeutic antibodies—the coming of age; Btech, vol. 11 (1993).
Kinsey, B. et al; Efficient Conjugation of DTPA to an IgM Monoclonal Antibody in Ascites Fluid; Nucl. Med. Biol. vol. 15 No. 3 pp. 285–292 (1988).
Lambert, J. et al; Purified Immunotoxins that are Reactive with Human Lymphoid Cells, Journal of Bilogical Chemistry, vol. 260, No. 22, pp. 12035–122041 (1985).
Kurantsin–Mills, J. et al; Indium–111 Oxine Labeled Erythrocytes: Cellular Distribution and Efflux Kinetics of the Label, Nucl. Med. Biol. vol. 16, No. 8, pp. 821–827 (1989).
Magnani, M. et al; Preparation and characterization of biotinylated red blood cells, Biotechnol. Appl. Biochem, vol 20, pp. 335–345, (1990).
Magnani, M. et al; Red Blood Cells as an Antigen–Delivery System; Biotechnol. Appl. Biochem, vol. 16, pp. 188–194 (1992).
Proulx, A. et al; A Kit for Labelling Erthrocytes or Leukocytes with Technitium–99m, Nucl. Med. Biol. vol. 17, No. 5, pp. 515–517 (1990).
Samokhin, G. et al; Red blood cell targeting to collagen–coated surfaces, Febs Letters, vol. 154, No. 2, pp. 257–261 (1983).
Schlom, J. Monoclonal Antibodies: They're More and Less Than You Think; Molecular Foundations on Oncology, pp. 95–134, (1991).
Suzuki, T. et al; Biotinylated Erythrocytes: In Vivo Survival and In Vitro Recovery, Blood. vol. 70, No. 3, pp. 791–795 (1987).
Taylor, R. et al. In Vivo Binding and Clearance of Circulating Antigen by Bispecific heteropolymer–Mediated Binding to Primate Erythrocyte Complement Receptor, Journal of Immunology, vol. 148, No. 8, pp. 2462–2468 (1992).
Taylor, R. et al; Use of heteropolymeric monoclonal antibodies to attach antigens to the C3b receptor of human, erythrocytes: A potential therapeutic treatment, Proc. Natl. Acad. Sci, USA, vol. 88, pp. 3305–3309 (1991).
Coller, Barry S., et al: Thromboerythrocytes In Vitro Studies of a Potential Autologous, Semi–artifical Alternative to Platelet Transfusions, J. Clin. Invest. vol. 89, pp. 546–555 (1992).
Kinsey, BM. et al. 1988. Nucl. Med. Biol. 15: 285–292
Christian, JA. et al. 1993, Blood 82:3469–3473.
Y. Collet, B. et al. Cancer Immunol. Immunother, 26:237–242, 1988.

*Primary Examiner*—Julie Burke
*Attorney, Agent, or Firm*—Limbach & Limbach L.L.P.

[57] ABSTRACT

First and second compounds are provided, where the first compound is administered to a mammalian host into blood for covalent bonding to blood components, where the components have an extended lifetime in the blood stream. The first compound comprises an active functionality and an agent of interest or a first binding entity. A second compound may be subsequently administered to the patient, which comprises a second binding entity, complementary to the first binding entity and an agent of interest. By virtue of binding to long-lived blood components, the half-life of the agent of interest is greatly extended in vivo.

6 Claims, No Drawings

CELLULAR AND SERUM PROTEIN ANCHORS AND CONJUGATES

This is a continuation of application Ser. No. 08/237,346 filed May 03, 1994, issued as U.S. Pat. No. 5,612,034 which is a continuation-in-part of Ser. No. 08/137,821, filed Oct. 15, 1993 now abandoned which was a continuation-in-part of Ser. No. 08/070,092 filed May 27, 1993, now abandoned, which is a continuation-in-part of Ser. No. 07/592,214 filed Oct. 3, 1990, now abandoned.

TECHNICAL FIELD

The field of this invention is agent, particularly therapeutic agent, delivery in a mammalian host.

BACKGROUND

Delivery of therapeutic agents to a mammalian host can frequently be as important as the activity of the drug in providing effective treatment. For the most part, drugs are delivered orally, frequently initially at a dosage below the therapeutic dosage and by repetitive administration of the drug, the dosage is raised to a therapeutic level or a level exceeding the therapeutic level. In many cases, the fact of having a dosage above therapeutic level provides for adverse effects, since most drugs are not only effective for the intended purpose, but frequently have adverse side effects. Various proposals have been made to avoid these problems, such as slow-release capsules, depots, pumps, and the like. These various approaches have numerous short comings for general applications where one wishes to maintain the presence of a therapeutic agent at a therapeutic dosage for an extended period. Invasive procedures are frequently undesirable, requiring surgery for introduction of the delivery device, followed by subsequent removal. Where the delivery device is placed on the skin, the agent must be capable of transport across the skin at the desired rate. Slow release particles have a limited time span and when introduced into the blood stream will be rapidly phagocytosed.

For those therapeutic agents which must be administered by injection, the need to have repetitive injections is particularly undesirable. The need in many cases for self administration is particularly problematical and in many instances may require trained individuals for the administration. There is, therefore, a serious need for methodologies which would allow for extended administration of therapeutic agents, particularly in the blood stream, which can be easily administered and efficacy maintained for extended periods of time.

SUMMARY OF THE INVENTION

Methods and compositions are provided for delivery of agents in the blood stream of mammalian hosts, by initially providing a bolus of a first compound comprising a chemically reactive group and a first entity, which may be the active agent or a first binding entity. The first compound will react with active functionalities of blood components, so as to provide functionalized blood components in relation to the proportion of a particular blood component to the total amount of blood components, and the reactivity of the functionalities of the blood component. After a few days, the population of functionalized blood components will be related, as well, to the half-life of the blood component, making immunoglobulins a major functionalized component.

At any time, where the first entity is a binding entity, a second compound may be introduced into the blood stream, where the second compound comprises a second binding entity, which specifically binds to the first binding entity, and an agent of interest. By varying the linking assemblage between the blood component and the agent of interest, the rate of release of the agent from the blood component may be controlled. The agent of interest is maintained in the host blood stream based on the lifetime of the long lived blood component, as modified, to provide a substantially extended lifetime for the agent of interest.

DESCRIPTION OF SPECIFIC EMBODIMENTS

Methods and compositions are provided for delivery of agents, particularly therapeutic agents, where the agents have an extended half-life in the blood stream. The invention comprises using from one to two compounds: a first compound comprising a chemically reactive entity which is capable of forming covalent bonds with functionalities present on proteins, joined by a covalent bond or first linking group to an agent of interest or a first binding entity, which binding entity is capable of binding specifically to a reciprocal binding member, where the two members define a specific binding pair; and, when the first compound comprises a first binding entity, a second compound which comprises the reciprocal binding member of the first binding entity and an agent of interest joined by a linking group.

By introducing the first compound into the blood of the host, particularly the blood stream, the chemically reactive group will react with available functionalities of blood components, so as to create a population of vascular functionalized blood components. During the lifetime of the functionalized blood components, as appropriate, the second compound may be added, which will bind to the first binding entity. By linking the agent of interest to a long-lived blood component, a long-lived depot of the agent of interest is achieved. The life-time at a useful dosage will usually be at least 10 days, more frequently 15 days or more.

The primary mobile blood components which react are red blood cells, immunoglobulins, such as IgM and IgG, serum albumin, transferrin, p90 and p38, where the IgG and serum albumin have the longer half-lives.

|  | Mol. wt., kDa | Conc., mg/ml | Half-life, days |
| --- | --- | --- | --- |
| IgM | 600 | 1 | 5 |
| IgG | 160 | 10 | 23* |
| transferrin | 74–82 | 2.5 | 10 |
| serum albumin | 67 | 40 | 18 |

*IgG$_3$ has a half-life of 8 days

Usually, by day 5, IgG, serum albumin and red blood cells will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The first compound will comprise the active functionality, a linking group, and the agent of interest or first binding entity. The functionalities which are available on proteins are primarily amino groups, carboxyl groups and thiol groups. While any of these may be used as the target of the reactive functionality, for the most part, bonds to amino groups will be employed, particularly formation of amide bonds. To form amide bonds, one may use a wide variety of active carboxyl groups, particularly esters, where the hydroxyl moiety is physiologically acceptable at the levels required. While a number of different hydroxyl groups may be employed, the most convenient will be N-hydroxysuccinimide, and N-hydroxy sulfosuccinimide, although other alcohols, which are functional in an aqueous medium such as blood, may also be employed. In some cases, special reagents find use, such as azido, diazo, carbodiimide anhydride, hydrazine, dialdehydes, thiol groups, or amines to form amides, esters, imines, thioethers, disulfides, substituted amines, or the like. Usually, the covalent bond which is formed should be able to be maintained during the lifetime of the agent of interest, unless it is intended to be the agent release site.

A large number of bifunctional compounds are available for linking to entities. Illustrative entities include: azidobenzoyl hydrazide, N-[4-(p-azidosalicylamino)butyl]-3'-[2'-pyridyldithio)propionamide), bis-sulfosuccinimidyl suberate, dimethyl adipimidate, disuccinimidyl tartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl[4-iodoacetyl]aminobenzoate, glutaraldehyde, and succinimidyl 4-[N-maleimidomethyl]cyclohexane-1-carboxylate.

When one or both of the linking groups is permanent, the linking group(s) will not be critical to this invention and any linking group which is convenient, physiologically acceptable at utilized doses, and fills the requirements of the molecule, such as being stable in the blood stream, effectively presenting the agent of interest or first binding entity, allowing for ease of chemical manipulation, and the like, may be employed. The linking group may be aliphatic, alicyclic, aromatic, or heterocyclic, or combinations thereof, and the selection will be primarily one of convenience. For the most part, any heteroatoms will include nitrogen, oxygen, sulfur or phosphorus. Groups which may be employed include alkylenes, arylenes, aralkylenes, cycloalkylenes, and the like. Generally the linking group will be of from 0–30, usually 0–10, more usually of from about 0–6 atoms in the chain, where the chain will include carbon and any of the heteroatoms indicated above. For the most part, the linking group will be straight chain or cyclic, since there will normally be no benefit from side groups. The length of the linking group will vary, particularly with the nature of the agent of interest and the first binding entity, since in some instances, the agent of interest or the first binding entity may naturally have a chain or functionality associated with it. In some instances, amino acids, generally from 1–3 amino acids may serve as the linking chain, particularly where the carboxyl group of the amino acid may be the reactive functionality. Thus, the amino group may serve to bond to the agent of interest or first binding entity.

The length of the arms may be used to provide for flexibility, rigidity, polyfunctionality, orientation, or other characteristic for improved function of the molecule. The covalent linking group may be a functionality which has an unequal affinity for different blood proteins, or which has a high affinity for a given protein epitope or sequence, such as an IgG or albumin epitope.

The first binding entity will generally be a small molecule, where the molecule is likely to minimize any immune response. Thus, for the most part, the first binding entity will be haptenic, usually below about 1 kD and generally more than about 100 D preferably less than about 600 D. Any physiologically acceptable molecule may be employed, where there is a convenient reciprocal binding member. Thus, of particular interest is biotin, where avidin may be the reciprocal binding member, but other molecules such as metal chelates, molecules mimicking a natural epitope or receptor or antibody binding site, also may find use, where the reciprocal binding member may be an antibody or a fragment thereof, particularly a Fab fragment, an enzyme, a naturally occurring receptor, or the like. Thus, the first binding entity may be a ligand for a naturally occurring receptor, a substrate for an enzyme, or a hapten with a reciprocal receptor.

The manner of producing the first compound will vary widely, depending upon the nature of the various elements comprising the first compound. The synthetic procedures will be selected so as to be simple, provide for high yields, and allow for a highly purified product. Normally, the reactive functionality will be created as the last stage, for example, with a carboxyl group, esterification to form an active ester will be the last step of the synthesis, unless one wishes to deprotect some functionality of the agent of interest or the first binding entity as the last step.

Usually, the first compound when it comprises the first binding entity will have a molecular weight of at least about 200 D and not more than about 2.5 kD, usually not more than about 1.5 kD and frequently less than about 1 kD.

Illustrative compounds include N-hydroxysuccinimidyl biotin ester, N-hydroxysulfosuccinimidyl biotin ester, N-hydroxysulfosuccinimidyl ester of N-biotinyl 6-aminohexanoic acid, N-hydroxysulfosuccinimidyl ester of N-biotinyl 4-butyryl, 3-aminopropyl disulfide, and the like. A large number of water soluble biotin derivatives for functionalizing proteins are available and to the extent that such compounds have linkers which are physiologically acceptable, these compounds may find application in this invention.

The first compound will usually be administered as a bolus, but may be introduced slowly over time by transfusion using metered flow, or the like. Alternatively, although less preferable, blood may be removed from the host, treated ex vivo, and returned to the host. The first compound will be administered in a physiologically acceptable medium, e.g. deionized water, phosphate buffered saline, saline, mannitol, aqueous glucose, alcohol, vegetable oil, or the like. Usually a single injection will be employed although more than one injection may be used, if desired. The first compound may be administered by any convenient means, including syringe, trocar, catheter, or the like. The particular manner of administration, will vary depending upon the amount to be administered, whether a single bolus or continuous administration, or the like. For the most part the administration will be intravascularly, where the site of introduction is not critical to this invention, preferably at a site where there is rapid blood flow, e.g. intravenously, peripheral or central vein. Other routes may find use where the administration is coupled with slow release techniques or a protective matrix. The intent is that the first compound be effectively distributed in the blood, so as to be able to react with the blood components.

For the most part, reaction will be with mobile components in the blood, particularly blood proteins and cells, more particularly blood proteins and red cells. By "mobile" is intended that the component does not haave a fixed situs. For the most part, reaction will be with plasma proteins, such as the immunoglobulins, particularly IgM and IgG, albumin, ferritin, and to a lesser degree other proteins which are present in substantially reduced amount. There may also be reaction with platelets, endothelial cells and white blood cells. There will, therefore, initially be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream. This means that after a few days, the agent of interest will be conjugated to, or the second compound will, for the most part, become conjugated with and bound to IgG.

In many situations, one may use a single first compound comprising the first binding entity, once such compound has been thoroughly tested in hosts, particularly human hosts, since its physiology will be well established, its pharmacokinetics will be established, and its safety over an extended period of time may be also established. In some instances the first compound will be physiologically and/or therapeutically active, where it may find use independent of addition of the second compound. However, to the extent that there may be idiosyncratic individuals, or that chronic administration of the first compound may result in some immune reaction, it may be desirable to have more than one first compound to be used for administration. However, since the role of the first compound may be somewhat restricted when used in combination with a second compound, it is not necessary that one develop numerous alternatives, although there will be numerous alternatives which will be useful for the same purpose.

For the most part, the half-life of the first compound will be at least about five days, more usually at least about 10 days and preferably 20 days or more. The period for providing an effective concentration may be much longer, since one may introduce a substantial excess of the first compound so that even after two or three half-lives, there may still be a useful amount of the first compound in the blood stream.

Generally, it will be satisfactory to have the agent of interest as part of the first compound. However, there will be situations where it will be desirable to use the combination of the first and second compounds. For example, if one wishes to have a relatively homogeneous population of components carrying the agent of interest, one can wait till the short lived blood components have dissipated, before adding the second compound. Particularly, where the initial concentration of the first compound may be high, it may be desireable to add the second compound subsequently which will primarily bind to the first compound, rather than react with a variety of blood components. In some instances the synthesis of the first compound with the agent of interest may be difficult, due to the highly functionalized nature of the agent of interest. This could be particularly true with oligopeptides which are synthesized and require removal of protecting groups at the end of the synthesis. Also, where the agent of interest is to be released from the blood component, it may be easier to design a combination of first and second compounds which allow for efficient release, rather than depending on the linking group of the first compound.

The dosage of the first compound will depend upon whether it comprises the agent of interest and will therefore be dependent on the adverse effects of the agent of interest, its activity when bound to blood components, the time necessary to reduce the free concentration of the first compound containing the agent of interest, the dosage necessary for therapeutic activity, the indication being treated, the sensitivity of the agent to blood enzymes, the route and mode of administration, and the like. As necessary, the dosage may be determined empirically, initially using a small multiple of the therapeutic dosage normally administered, and as greater experience is obtained, enhancing the dosage. Where the agent of interest is used to elicit an immune response, the agent of interest will be an antigen, and will not rely on the conjugation to the blood component for enhancing the immune response. In this case, relatively large dosages may be employed, where one is interested in producing antibodies as a product, where the treated host will normally be a domestic or laboratory animal. Where the agent of interest is acting as a vaccine, the dosage may be smaller and may be determined empirically. For the most part, as a vaccine the dosage will generally be in the range of about 10 ng to 100 μg. Normally, any additional dose will be administered after the original dose has been diminished by at least 50%, usually at least 90%, of the original dose.

As compared to the first compound, in some ways, the second compound may be much more sophisticated. This compound will have a second binding entity, which will be determined by the nature of the first binding entity. As already indicated, this entity may take numerous forms, particularly as binding proteins, such as immunoglobulins and fragments thereof, particularly Fab, Fv, or the like, particularly monovalent fragments, naturally occurring receptors, such as surface membrane proteins, enzymes, lectins, other binding proteins, such as avidin or streptavidin, or the like.

Particularly where the first binding entity is used with a second compound, the first binding entity will be naturally found at low concentration, if at all, in the host blood stream, so there will be little if any competition between the first binding entity and naturally occurring compounds in the blood for the second binding entity. The second binding entity should not bind to compounds which it may encounter in the blood or associated cells. Therefore, enzymes which are used will usually be active on substrates which do not appear in the blood. Lectins which are used will usually bind to sugars which do not appear in the blood and are not present on endothelial or other cells which line the vascular system.

For the most part, the second binding entity will be a protein, although other molecules which can provide for relatively high specificity and affinity may also be employed. Combinatorial libraries afford compounds other than proteins which will have the necessary binding characteristics. Generally, the affinity will be at least about $10^{-6}$, more usually about $10^{-8}$, e.g. binding affinities normally observed with specific monoclonal antibodies. Of particular interest is avidin or streptavidin, although other receptors of particular interest include receptors for steroids, TSH, LH, FSH, or their agonists, as well as sialic acid and viral hemagglutinins, and superantigens. The second binding entity will usually be a macromolecule, generally of at least about 5 kD, more usually of at least about 10 kD and usually less than about 160 kD, preferably less than about 80 kD, which may be mono- or divalent in binding sites, usually monovalent.

One or more agents of interest may be present in the first or second compound, usually multiple agents of interest being bound through first or second linking groups to a central core, e.g. a protein, nucleic acid, polysaccharide, or other multifunctional entity. Not only does a linking group serve to covalently bond the agent of interest, but it also serves to determine whether the agent of interest remains bound to the blood component or if released, the manner and rate of release. Therefore, the nature of the linking group will vary widely depending upon its role.

Where the agent of interest is to be retained bound to the blood component, any of a wide variety of convenient linking groups, including a bond, may be employed. Thus, the same types of linking groups employed in the first compound will find acceptance for the second compound.

However, where the linking group is to be cleaved and release the agent of interest, the linking group will vary depending upon the nature of the agent of interest, the desired rate of release, the valency or the functionality on the agent of interest which is to be released, and the like. Thus, various groups may be employed, where the environment of the blood, components of the blood, particularly enzymes, activity in the liver, or other agent may result in the cleavage of the linking group with release of the agent of interest at a reasonable rate.

Functionalities which may find use include esters, either organic or inorganic acids, particularly carboxyl groups or phosphate groups, disulfides, peptide or nucleotide linkages, particularly peptide or nucleotide linkages which are susceptible to trypsin, thrombin, nucleases, esterases, etc., acetals, ethers, particularly saccharidic ethers, or the like. Generally, the linking group for cleavage will require at least two atoms in the chain, e.g. disulfide, and may require 50 atoms, usually not more than about 30 atoms, preferably not more than about 20 atoms in the chain. Thus, the chain may comprise an oligopeptide, oligosaccharide, oligonucleotide, disulfide, organic divalent groups which are aliphatic, aromatic, alicyclic, heterocyclic or combinations thereof, involving esters, amides, ethers, amines, or the like. The particular linking group will be selected in accordance with physiological acceptance, desired rate of cleavage, synthetic convenience, and the like.

The disclosed therapeutic methods are applicable to a broad range of target entities, both host derived and foreign (meaning exogenous or non- host), which may be present in the blood and have a deleterious physiological effect, due to an undesirably high effective concentration, or as in the case of neoplastic cells, being present in any amount. Host derived cellular target entities include, (with parenthetical examples of clinical indication): T cells or subsets, such as CD2+, CD7+, CD4+, CD8+, CD25+ or LFA1+ cells (autoimmune disease, alloreactivity and inflammation), B cells or subsets such as pre-B cells, such as CD5+, IgE+, IgM+ etc. (B cell lymphoma, xenograft, autoimmunity, anaphylaxy), leukocytes, such as macrophages and monocytes (inflammation, myelomonocytic leukemia), other leukocytes such as neutrophils, basophils, NK cells, eosinophils, or allo- or xeno-reactive leukocytes, etc. (inflammation, anaphylaxis), stem cells such as CD34+ cells (polycythemia), malignant cells (malignancies; CALLA) or infected cells, particulaly HIV infected host cells, or the like.

Host derived non-cellular target entities include soluble HLA, class I and class II, and non-classical class I HLA (E, F and G) for modulating immunoregulation, soluble T or B cell surface proteins, cytokines, interleukins and growth factors, such as individually IL1–16, soluble IL2 receptor, M-CSF, G-CSF, GM-CSF, platelet derived growth factor, alpha, beta, and gamma interferons, TNF, NGFs, arachidonic acid metabolites such as prostaglandins, leukotrienes, thromboxane and prostacyclin for cardiovascular diseases, immunoglobulins such as total IgE for anaphylaxy, specific anti-allergen IgE, auto- or allo-antibodies for autoimmunity or allo- or xenoimmunity, Ig Fc receptors or Fc receptor binding factors, erythropoietin, angiogenesis factors, adhesion molecules, MIF, MAF, complement factors, PAF aceter, ions such as calcium, potassium, magnesium, aluminum, iron, etc, enzymes such as proteases, kinases, phosphatases, DNAses, RNAses, lipases and other enzymes affecting cholesterol and other lipid metabolism, esterases, dehydrogenases, oxidases, hydrolases, sulphatases, cyclases, transferases, transaminases, atriopeptidases, carboxylases and decarboxylases and their natural substrates or analogs, superoxide dismutase, hormones such as TSH, FSH, LH, Thyroxine (T4 and T3), renin, insulin, apolipoproteins, LDL, VLDL, dehydroepiandrosterone, cortisol, aldosterone, estriol, estradiol, progesterone, testosterone, dehydroepiandrosterone (DHEA) and its sulfate (DHEA-S), calcitonin, parathyroid hormone (PTH), human growth hormone (hGH), vasopressin and antidiuretic hormone (ADH), prolactin, ACTH, LHRH, THRH, VIP, cathecolamines (adrenaline, vanillylmandelic acid, etc.), bradykinins and corresponding prohormones, metabolites, ligands or natural cell or soluble receptors thereof, cofactors including atrionatriuretic factor (ANF), vitamins A, B, C, D, E and K, serotonin, coagulation factors, e.g. thrombin, fibrin, fibrinogen, Factor VIII, Factor XI, von Willebrand factor, tissue plasminogen activator, or other factors, complement activation factors, LDL and ligands thereof, uric acid, etc..

Foreign target entities include drugs, especially drugs subject to abuse such as heroin and other opiates, PCP, barbiturates, cocaine and derivatives thereof, benzodiazepins, etc., poisons, toxins such as heavy metals like mercury and lead, chemotherapeutic agents, paracetamol, digoxin, free radicals, arsenic, bacterial toxins such as LPS and other gram negative toxins, Staphylococcus toxins, Toxin A, Tetanus toxins, Diphtheria toxin and Pertussis toxins, plant and marine toxins, virulence factors, such as aerobactins, radioactive compounds or pathogenic microbes or fragments thereof, including infectious viruses, such as hepatitis A, B, C, E and delta, CMV, HSV (type 1, 2 & 6), EBV, varicella zoster virus (VZV), HIV-1, -2 and other retroviruses, adenovirus, rotavirus, influenzae, rhinovirus, parvovirus, rubella, measles, polio, reovirus, orthomixovirus, paramyxovirus, papovavirus, poxvirus and picornavirus, prions, protists such as plasmodia, toxoplasma, filaria, kala-azar, bilharziose, entamoeba histolitica and giardia, and bacteria, particularly gram-negative bacteria responsible for sepsis and nosocomial infections such as *E. coli*, Acynetobacter, Pseudomonas, Proteus and Klebsiella, but also gram positive bacteria such as *staphylococcus, streptococcus*, etc. Meningococcus and Mycobacteria, Chlamydiae, Legionnella and Anaerobes, fungi such as Candida, *Pneumocystis carini*, and Aspergillus, and Mycoplasma such as Hominis and *Ureaplasma urealyticum*.

The agent of interest may be varied widely, including naturally occurring compounds, synthetic compounds, and combinations thereof. Thus, a wide variety of compounds may be of interest, where the drug binds to a surface membrane receptor, so as to induce a signal. Alternatively, antagonists may be employed which will reduce the level of effective binding of the naturally occurring ligand. As agonists or antagonists, peptides and proteins include hormones, e.g. glucagon, insulin, TSH, LH. FSH, cytokines, e.g. IL-1, 2, 3, 4, 5, 6, 7, 8, 9, 10, 11, 12, 13, 14, 15, and 16, colony stimulating factors, e.g. G-, M- and GM-, immunoglobulins to specific ligands, where the ligand may be any hapten or antigen of interest, blood proteins, anticoagulants, e.g. heparin, and the like. The immunoglobulins are of particular interest, since they can provide for a wide variety of therapies, associated with infectious diseases, oncology, inflammation, immunological disorders, toxicology, and the like. The antibodies may be allogeneic or xenogeneic, particularly mouse or rabbit, monoclonal or polyclonal, particularly monoclonal, and may be modified antibodies, where the constant region, by itself, or in conjunction with the conserved framework segments in the variable region are modified to conserved human sequences.

Other compounds of interest, may be sugars, particularly oligosaccharides, which may bind to lectin domains to inhibit binding of naturally occurring substances, e.g. leukocyte binding to high endothelial venules, or other trafficking, nucleic acids, synthetic organic compounds, which are known to have therapeutic activity, such as antibiotics, antihypertensive agents, anti-coagulants, analgesics, hormones, chemotherapeutic agents, immunosuppressive or immunoregulatory agents, enzymes, vasoactive drugs, anti-inflammataory drugs, anti-histamines, etc.

Of particular interest are synthetic drugs, particularly drugs which act as impermeant drugs, such as antibiotics, adrenergic agonists and antagonists, cardiovascular drugs, antiproliferative drugs, diuretics, as well as some of the drugs listed above.

For the most part, the second compound will be administered in a bolus, where the concentration will depend upon the particular nature of the agent of interest. The dosage may be much higher than normal dosage for a particular agent, where the binding of the agent to the linking group substantially inactivates the agent. In this manner, the agent is only active upon release. Where the agent remains bound to the linking group, the dosage will be dependent upon the effective dosage of the agent as complexed with the first compound. The second compound may be administered substantially in the same manner as the first compound.

Because of the extended delivery time or availability of the subject agents, the subject invention may be used in a wide variety of situations. The second agent may be an antibody to a toxin, where there is concern about nosocomial infection in a hospital or other situation where disease may be spread. The subject invention may be employed before surgery so as to ensure that a level of drug is maintained during and subsequent to the surgery without requiring repetitive administration, avoiding the disturbance of the patient. For example, one may use anticlotting agents, where the nature of the surgery and indication is susceptible to the formation of clots. One may use inhibitors of leukocyte homing to prevent perfusion injury. One may use the subject invention with cardiovascular drugs, where a patient is particularly susceptible during an extended period to myocardial infarction. Other treatments which will benefit from long term availability of drugs include hormonotherapy, infertility therapy, immunosuppressive therapy, neuroleptic therapy, drug of abuse prophylaxy, treatment of diseases caused by infectious agents, treatment of hemophilia, and the like.

By conjugating a biologically active agent of interest to IgG in the blood of a mammalian host, many advantages ensue, in providing for a new activity for the immunoglobulins, while retaining many of the desirable features of the immunoglobulins, in addition to the extended life-time. For example, the immunoglobulins will usually still have $F_c$ effector function, such as its role in complement fixation, or the action of antibody dependent cytotoxic cells, effect on inactivation and secretion, and the like. Similarly, serum albumin and other long lived serum proteins can act to inactivate target entities and aid in their rapid elimination. Thus, the blood components to which the agent of interest is bound impart their physiological activities to the activity of the agent of interest. In this way cellular targets may be inactivated or eliminated by having immunoglobulins directed to a cellular or soluble target or by coating the cellular or soluble target with blood proteins.

The following examples are offered by way of illustration and not by way of limitation.

EXPERIMENTAL

I. Two rabbits were injected with a solution of N-succinimidyl biotin ester (NHS-biotin)(5 or 50 mg in 200 μl or 1 ml of DMSO) i.v. on day 0. Blood samples were taken at initially hourly, followed by daily intervals and the samples analyzed for the presence of biotin by gel electrophoresis (SDS-PAGE) employing 60 μg of sample, detecting the proteins to which biotin is bound by avidin-peroxidase conjugate, using a luminescent substrate (ECL kit, Amersham). For biotin bound to red blood cells, the cells were isolated by centrifugation, washed, lysed by hypotonic lysis, and the proteins separated by SDS-PAGE in the same manner as the plasma proteins. For the plasma proteins, the electrophoresis was run under reducing and non-reducing conditions, where the IgM and IgG were reduced to subunits under the reducing conditions.

The gels for the plasma proteins of one of the rabbits showed that biotin was bound to IgM, IgG, p90, p75 (transferrin), serum albumin, and p38. The duration for serum albumin for detection in the gel electrophoresis under reducing conditions was 9 to 12 days for the serum albumin, and up to 33 days for IgM and IgG, while for the non-reducing conditions, where the time for exposure was substantially less, bands could be observed for the serum albumin for 2 days and for the IgG for 9 days. With the red blood cells, a number of proteins could be observed for 12 days, the next point being 33 days, at which time no bands could be observed. The major labled component had an electrophoretic pattern suggesting Band 3.

II. To demonstrate that the subject invention can be used to enhance the immune response to a heterologous protein, after adminstration of the biotin conjugate as described above, 250 μg or 1 mg of egg white avidin was injected intravenously into each of two rabbits. Within about 2 days the titer began to rise rapidly and by 10 days a high anti-avidin titer was observed by ELISA, using avidin coated to microiplates, as evidenced by an OD value of about 600. By comparison, when avidin was administered as described above to rabbits to which the biotin conjugate had not been previously administered, there was substantially no production of antibodies until an intravenous booster injection of 50 μg of avidin was made on day 6, at which time there was a rapid increase in anti-avidin titer, approximating the titer observed with the biotin conjugate modified rabbits by day 12.

It is evident from the above results, that the subject invention provides for extended half-lives of agents for use in mammalian patients. Thus, agents which allow for prophylaxis or therapy can be administered to a patient, so as to become bound to long-lived components of blood where the lifetime of the agent is substantially extended. In this manner, frequency of administration can be substantially diminished, continued therapeutic benefit over extended periods of time is provided, the patient need not be repetitively disturbed for repeated administrations, and one can be assured that the agent is retained at a therapeutic dosage during the period of treatment.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated blood composition comprising:

conjugates of immunoglobulins and serum albumin covalently bonded to a synthetic organic compound as a biologically active compound as the major protein conjugates in said blood composition, said conjugates resulting from the addition of said synthetic organic compound to blood, said synthetic organic compound comprising (a) a reactive functional group which reacts with proteins to form stable covalent bonds, and either (b) a biologically active compound of interest, or (c) a first binding member which is a member of a specific binding pair consisting of said first binding member and a complementary second binding member.

2. A blood composition according to claim 1, wherein said first binding member of a specific binding pair is biotin.

3. A blood composition according to claim 2, wherein said complementary second binding member is avidin or streptavidin.

4. A blood composition according to claim 1, wherein said addition of said synthetic organic compound to blood occurs ex vivo.

5. A blood composition according to claim 1 wherein said addition of said synthetic organic compound occurs in vivo.

6. The composition of claim 1 wherein said reactive functional group is selected from the group consisting of N-hydroxysuccinimide and N-hydroxysulfosuccinimide.

* * * * *